United States Patent [19]
Spiva

[11] Patent Number: 4,686,712
[45] Date of Patent: Aug. 18, 1987

[54] GOGGLE MOUNTING SYSTEM

[76] Inventor: Lowell E. Spiva, 5778 Firebird Ct., Camarillo, Calif. 93010

[21] Appl. No.: 906,288

[22] Filed: Sep. 11, 1986

[51] Int. Cl.$^4$ .......................... A61F 9/00; A42B 1/04
[52] U.S. Cl. ............................................ 2/10; 2/202; 2/431; 2/427; 2/421
[58] Field of Search ...................... 2/10, 68, 421, 427, 2/431, 451, 452, 202, 205

[56] References Cited

U.S. PATENT DOCUMENTS

| | | | |
|---|---|---|---|
| 2,814,043 | 11/1957 | Alesi | 2/421 |
| 2,903,700 | 9/1959 | Finken et al. | 2/427 X |
| 3,577,564 | 5/1971 | Hill | 2/10 |
| 3,613,115 | 10/1971 | Hill | 2/10 |
| 3,691,565 | 9/1972 | Galonek | 2/431 |
| 4,573,217 | 3/1986 | Reed | 2/202 X |

FOREIGN PATENT DOCUMENTS 2306648 12/1976 France ...................... 2/202

Primary Examiner—Louis K. Rimrodt
Assistant Examiner—J. L. Olds
Attorney, Agent, or Firm—Koppel & Harris

[57] ABSTRACT

The goggle mounting system comprises protective goggles which carry one strap on each side for attachment to a helmet. The straps are flexible and resilient. The attachment of the straps to the helmet is such that the strap on only one side is easily disconnectable, while the strap on the other side is pivoted to the helmet and remains connected. The strap fasteners differ from one another in that one strap is attached to the helmet by means of mating sections of Velcro, respectively attached to the side of the helmet and the other fixedly attached to the strap. The other strap is attached to the helmet by a resilient snap fixed to the helmet and a mating member on the end of the strap.

23 Claims, 4 Drawing Figures ial
GOGGLE MOUNTING SYSTEM

BACKGROUND OF THE INVENTION

This invention is directed to a goggle mounting system which includes a pair of straps which are each attached to a cyclist's goggles at one end. They are attached at the other end to a helmet by attachment means, one strap being rotatably attached, the other strap being removably attached.

There are many types of goggles on the market for use either independently of or in combination with a helmet for various needs, including those where the user wears both a protective helmet and finds goggles helpful in protecting his eyes. Such users are dirt bike motorcyclists, dunebuggy drivers and passengers, and the like. Some of these goggles have straps which completely encircle the wearer's head. He can put on the goggles before the helmet, and, in this case, the goggles cannot be adjusted until the helmet is removed. If he places the goggle strap over the helmet, the wearer often has trouble putting the goggles in place, especially if the helmet has a visor and/or chin protector. Other goggles are arranged to snap directly on the helmet, but these are limited as to adjustability; and the manner in which they are attached to the helmet inhibits their adjustability, their attachment, and their detachment during driving. Thus, there is need for a goggle apparatus which allows for quick connecting and disconnecting and ease of adjustment.

SUMMARY OF THE INVENTION

The present invention is directed to a goggle apparatus which, when worn by the cyclist, allows for rapid adjustment as well as placement on or removal from the wearer's face when circumstances warrant such change due to temperature, moisture, sweat, or dirt in reaction to changes in terrain, wind or weather. It also allows the wearer to rapidly, with one hand only, disconnect the goggles from one side of the helmet while cycling. This permits the goggles to pivot downwardly out of the wearer's way while maintaining firm attachment to the helmet. Thus, the wearer's attention is not diverted by his goggles away from traffic or road conditions, thereby allowing for optimum safety.

It is, thus, an object and advantage of this invention to provide a goggle mounting system which associates eye protective goggles with a head protective helmet in such a way that the goggles can be easily and securely put in place, adjusted and removed.

It is another purpose and advantage of this invention to provide a goggle mounting system wherein the user wearing a helmet can adjust his goggles with one hand, including retrieving them from the open position, engaging them across his eyes, adjusting them, and securing them in place, as well as readjusting and removing the goggles.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

DESCRIPTION OF THE PREFERRED EMBODIMENT

Figure 1:
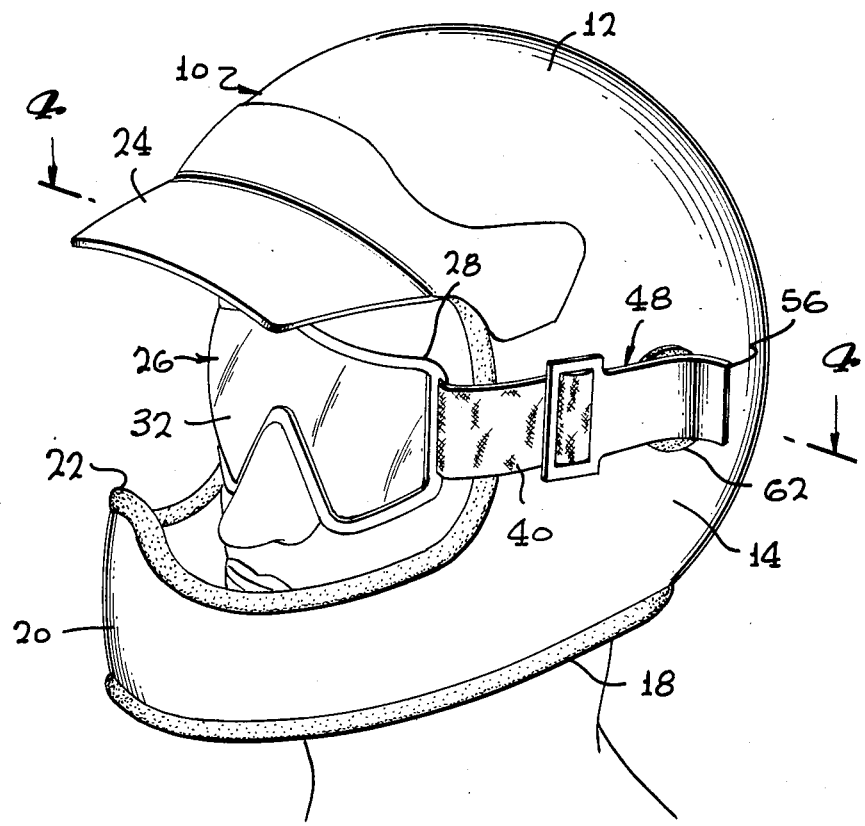
FIG. 1 is an isometric view of the goggle mounting system of this invention, showing it in association with goggles and a helmet on a user.

Helmet 10 is an example of a particular helmet style which is suitable for wearing when driving a motorcycle, including a dirt bike motorcycle, driving a dunebuggy, or as a passenger on either such type vehicle. Helmet 10 is characterized as having a crown 12 which has left side 14 which extends on the left side of the head, as seen by the wearer, and a right side 16 which extends down from the crown on the right side of the wearer's head. As is conventional, the crown extends down the back and joins the sides as a continuous member to protect the head of the wearer. The bottom of the helmet has a head opening 18 by which the wearer places the helmet on his head. In the helmet illustrated, chin guard 20 separates the head opening from the face opening 22. In addition, helmet 10 is provided with visor 24. It is to be understood that the helmet 10 is an example of a particular helmet style. The goggle mounting system of this invention is particularly useful on a helmet of that style, but it is also useful on helmets which are not provided with a chin guard which separates the head opening from the face and/or provided with a visor above the face opening. The interior of the helmet is provided with suitable supports and padding, as is customary in helmet construction, to protect the head it encloses.

Figure 2:
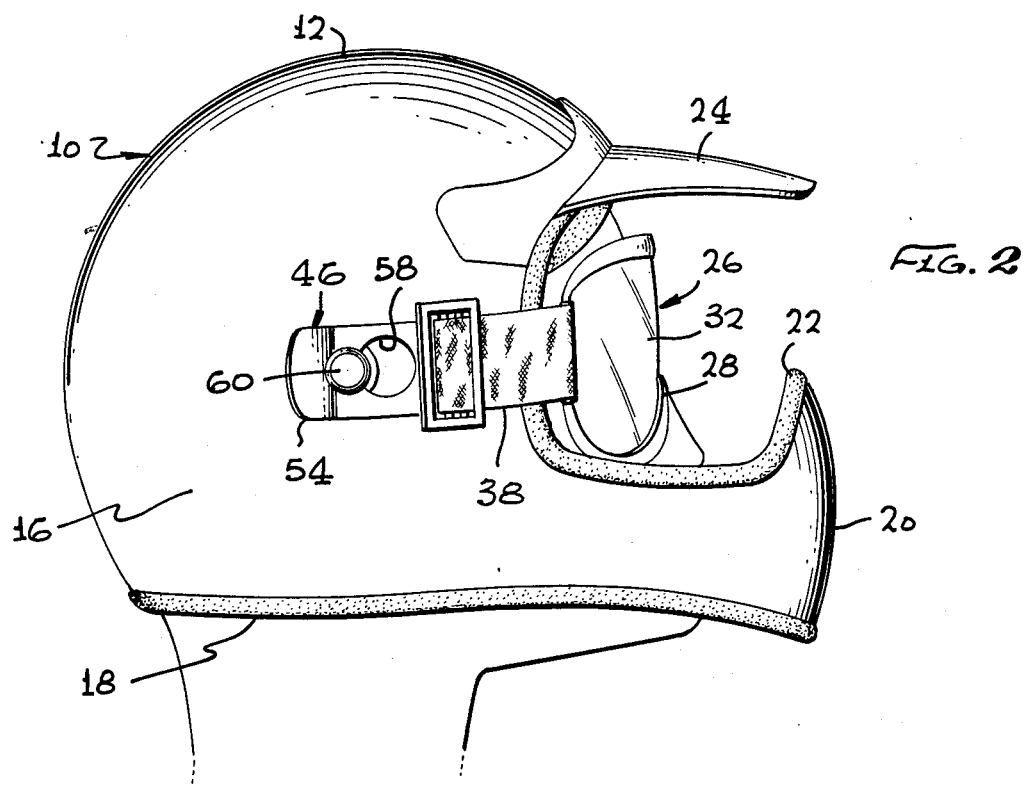
FIG. 2 is a side elevational view thereof with the goggles in place in the wearing position.
Figure 3:
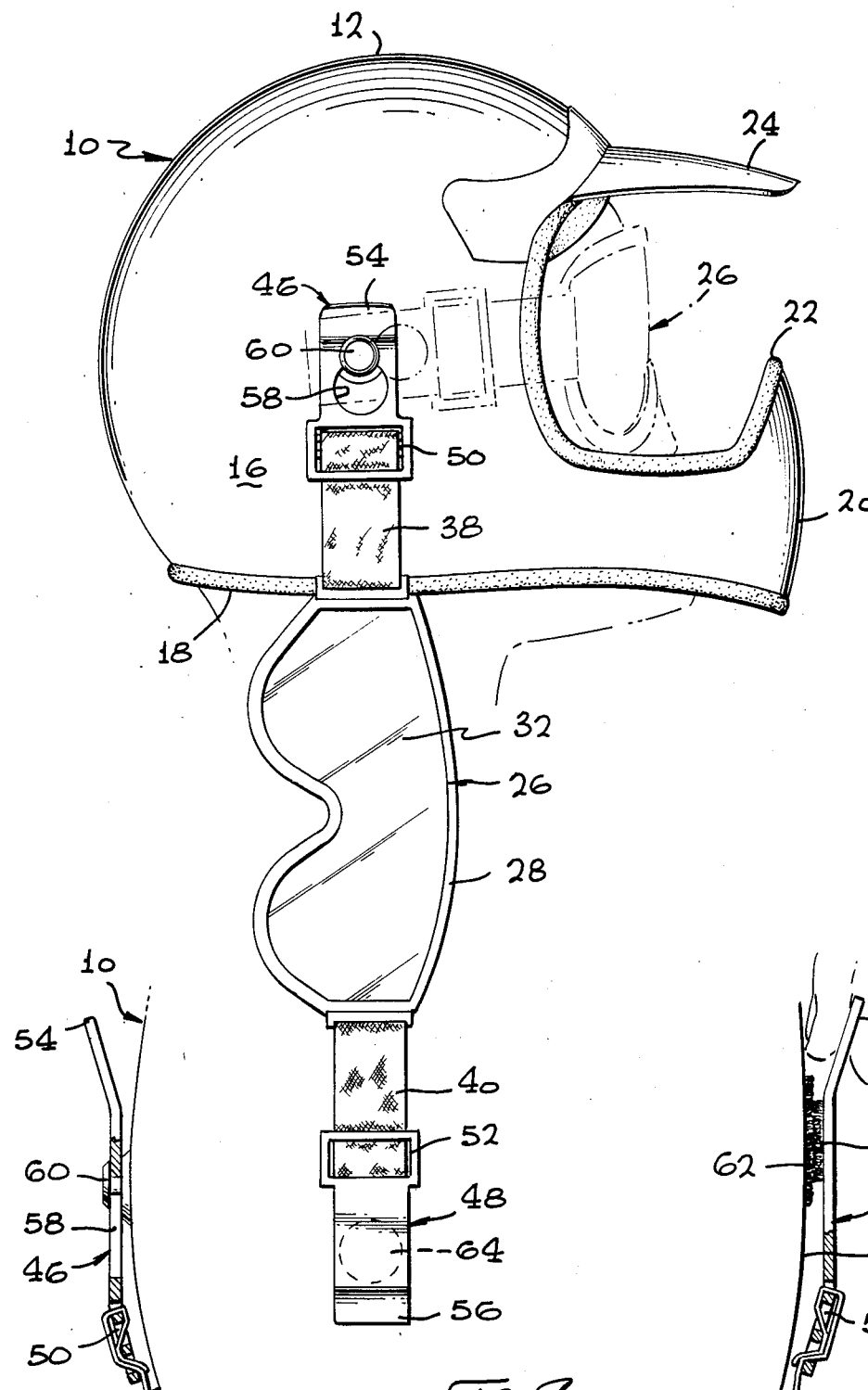
FIG. 3 is a view similar to FIG. 2 showing the goggles in the ready, non-wearing position.
Figure 4:
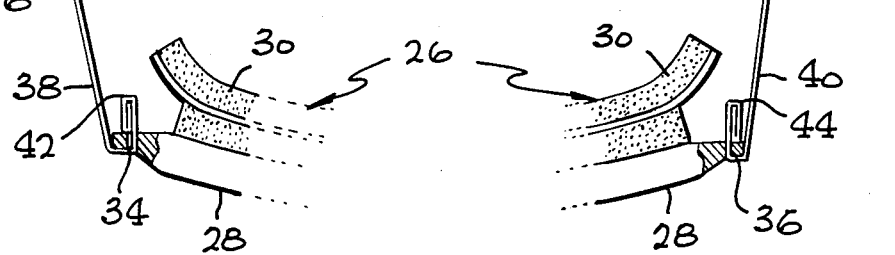
FIG. 4 is a downwardly looking view, as seen generally along the line 4—4 of FIG. 1, with parts broken away and parts taken in section.

Goggle 26, which is seen in FIGS. 1, 2, 3 and 4, has a frame 28 which is contoured to the wearer's face around his eyes and preferably carries padding 30 which seals the edges of the frame to the face and provides a sufficiently soft contact to be comfortable. One or two openings in the frame respectively carry one or two lenses 32 which enclose the openings in the frame and permit vision therethrough. For vision reasons, the lens 32 is transparent and may be tinted. As is best seen in FIGURE 4, slots 34 and 36 are formed at the outer edges of the frame 28 for receipt of goggle straps. Goggle straps 38 and 40 are respectively right and left goggle straps which have their forward ends respectively engaging through slots 34 and 36. The goggle straps have folded over and sewn ends 42 and 44 which are too thick to pass through the slots. In this way, the forward end of the goggle strap is secured in place. Goggle straps 38 and 40 are resilient straps, with built-in resilient longitudinal strength members. Right and left tabs 46 and 48 are critical parts of the goggle mounting system of this invention. The tabs are fairly stiff and are in the form of bars of substantially rectangular cross section. The tabs have a series of slots, with the slots 50 shown on tab 46 and the slots 52 shown on tab 48, so that the respective goggle straps 38 and 40 can be pulled therethrough so that each of the slots acts as a buckle for its respective goggle strap. The distance between each tab and its end of the goggle frame can be adjusted by pulling the strap through the slots. The forward end of the tabs, adjacent the slots, are turned inward to follow the contour of the helmet, as is best seen in FIG. 4. The rear end of the tabs is turned outward to form finger grips 54 and 56. As is seen in FIG. 4, these finger grips provide sufficient clearance from the sides of the helmet to be able to be engaged by the fingers. On the other hand, the finger grips should be turned out only the minimum necessary amount to prevent unnecessary protrusion. As is seen in FIG. 4, the tabs are configured to lie close to the sides of the helmet, with the finger grips turned out only enough to permit grasp. The tabs may be conveniently injection-molded of thermoplastic synthetic polymer composition material.

As seen in FIGS. 2, 3 and 4, right tab 46 has a keyhole slot 58 formed therethrough. The keyhole slot is formed of first and second circular openings which join each other with a common chord, which is smaller than the diameter of the smaller circle. Post fastener 60, see FIG. 4, has its base secured to the right side 16 of the helmet. Adhesive is a suitable fastening means. Post fastener 60 has a mushroom head which is larger than the small diameter in the keyhole, but smaller than the large diameter. Furthermore, the shank of the post between its base and head is of larger diameter than the chord between the two circles of the keyhole, but only slightly larger so that, with the resilient deflection of the tab, the post of fastener 60 can be snapped from the large circle to the small cirle of the keyhole opening, as well as in the opposite direction. When the post of the post fastener is in the small circle of the keyhole opening, the right tab 46 is considered to be attached to the post.

Tab 48 is detachably and adjustably secured to the left side of the helmet by means of two pieces of mating Velcro. These pieces are seen in FIG. 4 and are indicated at 62 and 64. The Velcro piece 62 is adhesively secured to the left side of the helmet, while the Velcro piece 64 is adhesively secured to the inside of tab 48.

A motorcyle rider must always keep his right hand on the handlebar to control the throttle as well as to steer. The control requirements by the hands of a dunebuggy driver are not quite so severe, but in rough terrain, he must firmly grasp the steering wheel in order to maintain control. For various reasons, the driver may want to remove or adjust his goggles, and when the goggles are not over his eyes, he may wish to place them in protective position over his eyes. FIGS. 1, 2 and 4 show the position wherein the goggles are in protective position. The tab 46 is engaged upon post 60, and the tab 48 is held in place by means of its Velcro. To remove the goggles, the driver can reach up with his left hand, engage left finger grip 56 with the fingers on his left hand, and pull the Velcro loose. If the driver wants to move the goggles away from his face, with his left hand he pulls the goggles forward and to the right lets them drop so that they hang on post fastener 60 by means of right tab 46. This position is shown in FIG. 3. They are out of the driver's way, but are readily accessible and are replaceable with one hand. When the driver wants to replace the goggles, he reaches across with his left hand and grasps tab 48 and finger grip 56, pulls the goggles across his face, and brings the tab 48 back to attach it by means of its Velcro. The original adjustments as to tension on the straps 38 and 40 is made before the driver starts out. Smaller adjustments can be made by the place of attachment of the Velcro piece 64 on the tab with respect to the Velcro piece 62 on the helmet. To facilitate adjustment, the helmet Velcro piece 62 may be made larger, as indicated. This provides small adjustment by the driver while he is operating his vehicle.

The goggle mounting system thus provides goggles which are particularly useful for off-road vehicle drivers and other persons who must place, remove, replace and adjust their goggles under adverse conditions while in use with one hand. The goggle mounting system is illustrated as being employed with a helmet having both a chin guard and a visor because, under these circumstances, the placement and replacement of goggles is most difficult because the face opening is smallest and most restricted. The goggle mounting system permits the driver to lift the goggles a small distance away from his face, should they become fogged up on the inside, to ventilate and remove the moisture from the interior of the goggles. Just as easily, he can make minor adjustments by securing the tab 48 at different positions on the Velcro, to tighten or loosen the goggles. Such adjustment may be useful during long runs, with changes in temperature, which would affect the fit of the goggles against the face and affect the elasticity of the goggle straps. The goggle mounting system of this invention thus permits quick, one-handed mounting and demounting of the goggles together with infinite adjustability of the goggle tightness during use in adverse conditions.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A goggle mounting system comprising:
first and second tabs;
said first tab having means thereon for attachment to the first strap of a two strap goggle and having separate means thereon for pivotal attachment to one side of a helmet, said attachment means enabling detachment of the first tab from the helmet but preventing detachment of the first tab when the first tab is pulled outward away from the helmet;
said second tab having means thereon for attachment to the opposite strap of the two strap goggle from the strap to which said first tab is attached, said second tab also having means thereon for nonpivotable attachment to an opposite side of a helmet, the attachment means for the second tab being positionally adjustable along the helmet for adjusting the tension on the goggle straps, and detachable from the helmet by an outward pull away from the helmet.

2. The goggle mounting system of claim 1 wherein said means for pivotally mounting said first tab with respect to a helmet comprises a post for attachment to the helmet and a surface on said first tab for pivotally engaging said post.

3. The goggle mounting system of claim 2 wherein said post has a base for adhesive attachment to a helmet and a mushroom head on said post with said post extending between said mushroom head and said base and said surface on said first tab engages said post.

4. The goggle mounting system of claim 3 wherein said surface on said first tab comprises a keyhole.

5. The goggle mounting system of claim 4 wherein said kekyhole surface comprises an opening larger than said mushroom head and a connected opening smaller than said mushroom head with the juncture between said openings being smaller than said post, said first tab being made of resilient material so that said post can be snapped from said larger opening into said smaller opening.

6. The goggle mounting system of claim 2 wherein said surface on said first tab comprises a keyhole.

7. The goggle mounting system of claim 6 wherein said means on said first tab for attachment of a goggle strap comprises buckle slots for multiple engagement by a buckle strap to secure the buckle strap and a goggle attached thereto to said first tab.

8. The goggle mounting system of claim 1 wherein said means on said first tab for attachment of a goggle strap comprises buckle slots for multiple engagement by a buckle strap to secure the buckle strap and a goggle attached thereto to said first tab.

9. The goggle mounting system of claim 1 wherein said second tab has a first piece of hook and pile fastener attached thereto and has a second piece of hook and pile fastener detachably attached to said first piece of hook and pile fastener, said second piece of hook and pile fastener being attachable to a helmet.

10. The goggle mounting system of claim 9 wherein said second tab has a finger grip thereon positioned for finger engagement when said second piece of hook and pile fastener is attached to the helmet.

11. The goggle mounting system of claim 10 wherein said means for attaching a goggle strap to said second tab comprises a plurality of buckle slots in said second tab for multiply engaging a buckle strap to attach to the buckle strap and to the goggle attached to the buckle strap.

12. The goggle mounting system of claim 10 wherein said means for pivotally mounting said first tab with respect to a helmet comprises a post for attachment to the helmet and a surface on said first tab for pivotally engaging said post.

13. The goggle mounting system of claim 12 wherein said post has a base for adhesive attachment to a helmet and a mushroom head on said post with said post extending between said mushroom head and said base and said surface on said first tab engages said post.

14. The goggle mounting system of claim 13 wherein said surface on said first tab comprises a keyhole.

15. The goggle mounting system of claim 14 wherein said keyhole surface comprises an opening larger than said mushroom head and a connected opening smaller than said mushroom head with the juncture between said openings being smaller than said post, said first tab being made of resilient material so that said post can be snapped from said larger opening into said smaller opening.

16. The goggle mounting system of claim 12 wherein said surface on said tab tab comprises a keyhole.

17. The goggle mounting system of claim 16 wherein said means on said first tab for attachment of a goggle strap comprises buckle slots for multiple engagement by a buckle strap to secure the buckle strap and a goggle attached thereto to said first tab.

18. The goggle mounting system of claim 1 wherein said goggle mounting system is in combination with a helmet having first and second sides with said first and second tabs respectively detachably mounted on said first and second sides of said helmet and further in combination with a goggle having first and second goggle straps, said first goggle strap being attached to said first tab and said second goggle strap being attached to said second tab.

19. The goggle mounting system of claim 7 wherein said goggle mounting system is in combination with a helmet having first and second sides with said first and second tabs respectively detachably mounted on said first and second sides of said helmet and further in combination with a goggle having first and second goggle straps, said first goggle strap being attached to said first tab and said second goggle strap being attached to said second tab.

20. The goggle mounting system of claim 9 wherein said goggle mounting system is in combination with a helmet having first and second sides with said first and second tabs respectively detachably mounted on said first and second sides of said helmet and further in combination with a goggle having first and second goggle straps, said first goggle strap being attached to said first tab and said second goggle strap being attached to said second tab.

21. The goggle mounting system of claim 17 wherein said goggle mounting system is in combination with a helmet having first and second sides with said first and second tabs respectively detachably mounted on said first and second sides of said helmet and further in combination with a goggle having first and second goggle straps, said first goggle strap being attached to said first tab and said second goggle strap being attached to said second tab.

22. A goggle mounting system for connecting goggles to a helmet comprising:
a goggle;
a helmet;
first and second flexible resilient straps, each of said straps having a goggle end and a helmet end, said goggle ends of both said first and second straps being connected to said goggles, each at an opposite end of said goggle;
means for releasably and rotatably attaching said first strap to one side of said helmet while preventing detachment of the first strap from the helmet by an outward pull away from the helmet; and
means for releasably and non-rotatably attaching said second strap to the other side of said helmet, said second strap attachment means being positionally adjustable along the helmet for adjusting the tension on the goggle straps in accordance with the position of the second strap attachment means on the helmet.

23. A goggle mounting system for connecting goggles to a helmet comprising:
a goggle, said goggle having first and second ends;
a helmet, said helmet having first and second sides;
first and second flexible and resilient straps, said first and second straps being respectively fixedly attached to said goggle respectively at said first and second ends of said goggle;
first and second tabs, said first and second flexible and resilent straps being respectively adjustably attached to said first and second tabs;
first attachment means for non-adjustably, pivotally and removably attaching said first tab to said first side of said helmet, said first attachment means comprising a post mounted on said first side of said helmet releasably engaging in a keyhole opening in said first tab, whereby said first tab is held on the helmet against outward pulling away from the helmet;

second attachment means for releasably, adjustably and non-rotatably attaching said second tab to said second side of said helmet, said second attachment means comprising first and second mating hook and eye fastener pieces, one of said hook and eye fastener pieces being fixedly attached to said second side of said helmet and the other of said hook and eye fastener pieces being fixedly attached to said second tab so that said second tab can be detached, adjusted and attached with respect to said helmet.

* * * * *